United States Patent [19]
Gyory et al.

[11] Patent Number: 5,234,992
[45] Date of Patent: Aug. 10, 1993

[54] ELECTROTRANSPORT ADHESIVE

[75] Inventors: J. Richard Gyory, Los Altos; Ronald P. Haak, Cupertino; Felix Theeuwes, Los Altos; Patrick J. Lew, Mountain View, all of Calif.

[73] Assignee: ALZA Corporation, Palo Alto, Calif.

[21] Appl. No.: 308,716

[22] Filed: Feb. 9, 1989

[51] Int. Cl.[5] .................................. C08G 63/91
[52] U.S. Cl. ................................. 525/57; 525/58; 525/59; 525/61; 525/931; 525/937; 525/941; 524/47; 524/52; 524/54; 524/55; 524/925; 604/20
[58] Field of Search .............. 604/20; 525/57, 58, 525/59, 61, 931, 937, 941; 524/47, 54, 52, 55, 925; 128/802

[56] References Cited

U.S. PATENT DOCUMENTS

| | | | |
|---|---|---|---|
| 2,624,690 | 6/1953 | Leader | 167/58 |
| 2,997,399 | 8/1961 | Eberhard et al. | 106/35 |
| 3,475,363 | 10/1969 | Gander | 260/29.7 |
| 3,564,078 | 2/1971 | Wicker et al. | 260/881 |
| 3,574,153 | 4/1971 | Sirota | 260/8 |
| 3,575,911 | 4/1971 | Peterson | 260/29.6 |
| 3,975,350 | 8/1976 | Hudgin et al. | 524/108 |
| 4,008,721 | 2/1977 | Burton | 128/418 |
| 4,082,705 | 4/1978 | Beede | 260/4 R |
| 4,140,115 | 2/1979 | Schonfeld | 128/156 |
| 4,141,359 | 2/1979 | Jacobsen et al. | 525/457 |
| 4,170,612 | 10/1979 | Pastor et al. | 525/101 |
| 4,181,635 | 1/1980 | Takamatsu | 260/5 |
| 4,226,915 | 10/1980 | Iijima et al. | 428/492 |
| 4,253,460 | 3/1981 | Chen et al. | 128/283 |
| 4,273,135 | 6/1981 | Larimore et al. | 128/640 |
| 4,274,420 | 6/1981 | Hymes | 128/641 |
| 4,356,819 | 11/1982 | Potaczek | 128/156 |
| 4,391,278 | 7/1983 | Cahalan et al. | 128/640 |
| 4,393,080 | 7/1983 | Pawelchak et al. | 525/389 |
| 4,393,150 | 7/1983 | Kresner | 523/111 |
| 4,456,741 | 6/1984 | Ames | 526/264 |
| 4,460,371 | 7/1984 | Abber | 604/897 |
| 4,474,570 | 10/1984 | Ariura et al. | 604/20 |
| 4,564,010 | 1/1986 | Coughlan et al. | 128/156 |
| 4,584,355 | 4/1985 | Blizzard et al. | 524/500 |
| 4,588,762 | 5/1986 | Mruk et al. | 524/49 |
| 4,655,767 | 4/1987 | Woodward et al. | 604/896 |
| 4,702,732 | 10/1987 | Powers et al. | 604/20 |
| 4,798,876 | 1/1989 | Gould et al. | 525/457 |
| 5,004,767 | 4/1991 | Krause et al. | 524/47 |
| 5,080,646 | 1/1992 | Theeuwes et al. | 604/20 |

FOREIGN PATENT DOCUMENTS 1216268 12/1970 United Kingdom .
2115431A 9/1983 United Kingdom .

Primary Examiner—John C. Bleutge
Assistant Examiner—Randy Gulakowski
Attorney, Agent, or Firm—D. Byron Miller; Edward L. Mandell; Steven F. Stone

[57] ABSTRACT

An adhesive composition suitable for use as an in-line contact adhesive for electrotransport drug delivery systems.

22 Claims, 1 Drawing Sheet

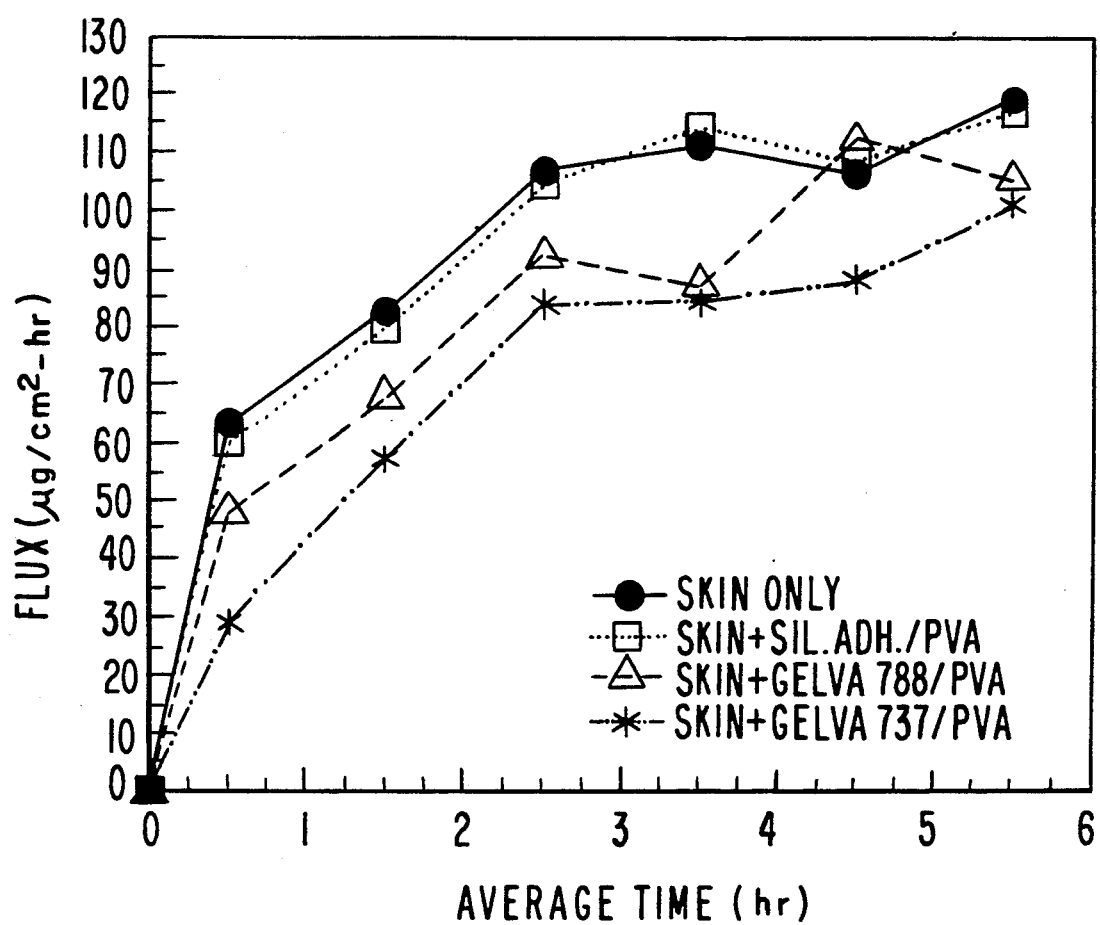

ELECTROTRANSPORT ADHESIVE

FIELD OF THE INVENTION

This invention relates to adhesive compositions. More particularly, this invention relates to adhesives for use as in-line contact adhesives for transdermal systems which deliver agents with electrical assistance. Still more particularly, but without limitation thereto, this invention relates to adhesives which permit the passage of water soluble and ionized agents.

DEFINITION OF TERMS

As used herein, the terms "electrotransport" and "electrically assisted transport" are used interchangeably and are defined as the mechanism by which drugs are transported through a biological interface under the influence of an electrical field. The term "biological interface" as used herein, is defined as including without limitation, skin, body tissues, mucosal membranes, nails and blood vessel walls. As used herein, the expressions "agent" and "drug" are used interchangeably and are intended to have their broadest interpretation as any therapeutically active substance which is delivered to a living organism to produce a desired, usually beneficial effect.

BACKGROUND OF THE INVENTION

Intimate contact with a body surface, skin for example, is especially desirable in electrotransport systems. Along with establishing an interface for ionic and/or water soluble species to diffuse, having intimate contact also insures uniform electrical current distribution, thereby avoiding high localized current densities which could cause damage to the body tissue to which the system is applied.

Important criteria for adhesive compositions utilized as in-line contact adhesives for transdermal drug delivery systems in general, are: sufficient tack for prolonged adhesion to a body surface, aggressiveness, cohesion, bio- and chemical-compatibility, rapid drug transport ability, mechanical flexibility and insolubility in water. When drugs are administered by electrotransport means rather than by passive diffusion, the adhesive must also have low resistance to ionic and water soluble drug transport and should not significantly contribute competing ionic species.

Adhesives for use with electrodes are well known in the art. Typical materials include: solvent activated adhesives such as a vinyl acrylic copolymer which is water insoluble and thus activated by acetone or a low molecular weight alcohol, U.S. Pat. No. 4,008,721, and polymerized 2-acrylamido-2-methylpropanesulfonic acid which is soluble in and thus activated by water, U.S. Pat. No. 4,391,278; and, adhesives such as karaya gum having an electrically conductive material such as an ionizable salt or a finely powdered metal dispersed therethrough, U.S. Pat. No. 4,274,420; all of which are incorporated herein by reference. While these adhesives are suitable for use when current alone is being transported, they are not necessarily suitable for use when drug is being transported, either because the solvent used may react adversely with or hinder the drug's delivery to a body surface, or because the constituents incorporated therein may interfere with drug transport. One attempt to solve this incompatibility was to incorporate drug into a self-adhering drug reservoir comprised of a gel formed from a hydrophilic natural or synthetic material such as a natural resinous polysaccharide, plasticized with water and/or polyols, U.S. Pat. No. 4,474,570, which is incorporated herein by reference. However, it is not always desirable to use a self-adhering drug reservoir and it is not always possible such as when there is a rate controlling membrane positioned between the drug reservoir and the skin.

This invention therefore provides an adhesive formulation which overcomes many of the disadvantages associated with state of the art adhesives and is particularly suited for use as an in-line contact adhesive in electrically assisted drug transport systems.

SUMMARY OF THE INVENTION

An object of this invention is to provide an adhesive formulation suitable for use as an in-line contact adhesive for electrically assisted drug delivery systems.

A further object of this invention is to provide an adhesive which has acceptable resistance to ionic transport when in a hydrated state.

A still further object of this invention is to provide an adhesive which provides for uniform charge distribution.

These and other objects, features and advantages of the invention have been demonstrated by the present invention wherein an ion-conducting adhesive for use in a transdermal agent delivery system where agent in an ionized or water soluble form is transported with electrical assistance, is comprised of a hydrophobic polymer having adhesive properties and which has water sorbable hydrophilic particles uniformly dispersed therethrough, where said particles provide pathways for passage of the ionized agent.

BRIEF DESCRIPTION OF THE DRAWINGS

The invention will be described in further detail to the accompanying drawing wherein:

The single FIGURE is a graph presenting the electrically assisted flux of metoclopramide through several adhesive formulations of this invention, adhered to skin.

DESCRIPTION OF THE INVENTION

This invention is a predominantly hydrophobic adhesive having aqueous pathways for use in transdermal drug delivery systems which utilize electrical current to facilitate drug delivery and wherein a hydrophobic polymer having adhesive properties is rendered hydrophilic to varying degrees by blending in hydrophilic particles. These particles are granular in nature, water sorbable and preferably non-ionic. The hydrophilic particles can be either water soluble or water insoluble. These particles function as a hydroattractant material, forming aqueous pathways in the polymer, through which the ionized or water soluble agent can pass through the adhesive.

The adhesive can be either in a dry or a hydrated state when applied to the biological interface, depending upon the delivery profile desired or depending upon the stability of the other constituents, for example the drug or electrodes, when water is present. Utilizing the adhesive in a hydrated state may facilitate the onset of drug delivery as the pathways for drug passage will be immediately available. Hydrating the adhesive can be accomplished in several ways. The adhesive can be hydrated before packaging or it can be hydrated immediately prior to placement on the biological interface. Alternately the aqueous source can be incorporated into the electrotransport drug delivery system with a barrier separating the source from the adhesive, said barrier being broken or removed immediately prior to use so as to hydrate the adhesive.

It may further be desirable to place a set amount of the agent to be delivered in the adhesive itself to provide a priming dose of agent when the system is placed on the biological interface. Alternately, the adhesive itself may be the drug reservoir to form a self adhering system. To function as a reservoir, the adhesive must contain agent is an amount sufficient to maintain therapeutic delivery for an extended period of time. The adhesive may also have other additives present such as are commonly known in the art. These include, plasticizers which may modify the tack and cohesive strength of the adhesive, fillers which may reduce the cost and improve handling, and antioxidants which improve the adhesive's resistance to oxidative degradation.

Blending of the hydrophobic and hydrophilic components is done mechanically, either in solution or by milling. No polymerization or chemical alteration takes place. The resulting adhesive films are then prepared by solvent casting or by melt processing.

State of the art adhesives which are comprised of hydrophobic polymers, normally are only capable of absorbing less than 2% of their own weight in water. The presence of water and the resulting aqueous pathways is critical to the success of this invention and the addition of hydrophilic particles to the hydrophobic polymer creates an adhesive which is capable of absorbing water within the range of 7-80% of the total adhesive weight.

The hydrophilic particles can be present within the range of 10-60 dry weight percent, with the preferred range being 30-40 dry weight percent. The adhesive further comprises about 50-80, preferably 60-70, weight percent of the hydrophobic polymer. A suitable amount of particles is that which provides sufficient hydrophilic pathways such that the resultant distribution is uniform, but does not significantly lower the strength of the adhesive. Keeping this criteria in mind, increasing the amount of particles will increase the current distribution but will also decrease the adhesive strength. The average particle diameter can be within the range of less than 38 $\mu$m up to 177 $\mu$m. The diameter selected is related to the thickness of the adhesive. For a 5 mil thick adhesive, the average particle diameter should be no larger than 125 $\mu$m. On the other hand, the preferred particle diameter for the typical 2-3 mil thick adhesives utilized with electrotransport systems is less than 38 $\mu$m.

The hydrophobic polymer itself can have adequate adhesive properties or it may be rendered adhesive by the addition of tackifying resins.

Suitable hydrophobic polymers include, without limitation, acrylic or methacrylic resins such as polymers of esters of acrylic or methacrylic acid with alcohols such as n-butanol, n-pentanol, isopentanol, 2-methyl butanol, 1-methyl butanol, 1-methyl pentanol, 2-methyl pentanol, 3-methyl pentanol, 2-ethyl butanol, isooctanol, n-decanol, or n-dodecanol, alone or copolymerized with ethylenically unsaturated monomers such as acrylic acid, methacrylic acid, acrylamide, methacrylamide, N-alkoxymethyl acrylamides, N-alkoxymethyl methacrylamides, N-tert. butylacrylamide, itaconicacid, vinylacetate, N-branched alkyl maleamic acids wherein the alkyl group had 10-24 carbon atoms, glycol diacrylates, or mixtures of these. Typical examples of commercially available acrylate adhesives suitable for use in this invention are the polyvinylacetate compounds sold by Monsanto Polymer Products Co. under the name of GELVA, such as GELVA 737 and GELVA 788, acrylate adhesives sold by the 3M Company such as 3M #9871 and 3M #9872, and sold by The Kendall Company under the name Kendall A200C-0. Also suitable are silicone adhesives which are prepared by the reaction of a linear polydimethylsiloxane fluid with a solvent soluble, low molecular weight silicate resin. A typical example of a silicone adhesive suitable for use in this invention is a medical grade of silicone pressure-sensitive adhesive commercially available under the trademark DOW CORNING ®355 Medical Grade Adhesive from Dow Corning Corporation. Plasticizers may also be added. A typical example is the addition of silicone medical fluid to the silicone adhesive.

Suitable hydrophobic polymers which can be rendered adhesive by the addition of tackifying resins include, without limitation, poly(styrenebutadiene) and poly(styrene-isoprene-styrene) block copolymers, ethylene vinyl acetate polymers such as those which are described in U.S. Pat. No. 4,144,317, plasticized or unplasticized polyvinylchloride, and natural or synthetic rubber, $C_2$-$C_4$ olefins such as polyethylene, polyisoprene, polyisobutylene and polybutadiene. Examples of suitable tackifying resins include, without limitation, fully hydrogentated aromatic hydrocarbon resins, hydrogenated esters and low molecular weight grades of polyisobutylene. Particularly suitable are tackifiers sold under the trademarks Staybelite Ester ® #5 and #10, Regal-Rez ® and Piccotac ®, all of Hercules, Inc. (Wilmington, Del.).

Suitable materials for the hydrophilic particles include, without limitation, polyacrylamide (PAA), Klucel ®, cross-linked dextran such as Sephadex (Pharmacia Fine Chemicals, AB, Uppsala, Sweden), polyvinylalcohol (PVA), Waterlock A-180 (Grain Processing Corp., Muscatine, Iowa) which is a starch-graft-poly(sodium acrylate-co-acrylamide)polymer, cellulosic derivatives such as hydroxypropylmethylcellulose (HPMC), low-substituted hydroxypropylcellulose (LHPC) and cross-linked Na-carboxymethylcellulose such as Ac-Di-Sol (FMC Corp., Philadelphia, Pa.), hydrogels such as polyhydroxyethyl methacrylate (pHEMA) (National Patent Development Corp.), blends of polyoxyethylene or polyethylene glycols with polyacrylic acid such as Polyox ® blended with Carbopol ®, cross-linked polyvinyl pyrrolidone (PVP) (GAF Corporation), natural gums and chitosan. Also suitable are phospholipids such as L-$\alpha$-phosphatidylcholine (Sigma Chemical Company) which has both hydrophilic and hydrophobic properties.

The adhesive made according to this invention is predominantly hydrophobic but has hydrophilic pathways in order to allow ions to pass through under the influence of an electric field, i.e., the adhesive presents minimal mass transport resistance. The adhesive also has good hydration kinetics so that the time it takes to absorb water and pass current, is acceptable. A suitable time to reach steady state moisture content is about 2-5 hours. Further, the adhesive layer provides for uniform current distribution so as to avoid highly localized current densities which could result in tissue damage.

The adhesive must have reasonable ionic conductivity so that it is not rate limiting nor does it require significant (greater than 100 mV at 0.1 mA/cm$^2$) voltage during system operation, i.e., the adhesive presents minimal electrical resistance. State of the art adhesives have been shown to be essentially blocking to ionic transport in that ions are unable to pass through the adhesive. By incorporating hydrophilic particles, the adhesive of this invention has been shown to exhibit resistivity of less than 1 kohm-cm$^2$ for a typical 3 mil thick sample, or less than 0.33 kohm-cm$^2$ per mil thickness of adhesive.

Having thus generally described our invention, the following examples will illustrate how variations of the above described parameters provide adhesives suitable for use as in-line contact adhesives for electrotransport systems.

EXAMPLE I

Several acrylate-based adhesive formulations were tested in vitro to evaluate the electrically assisted and passive transport of the drug metoclopramide. Adhesive samples 5mils in thickness were laminated onto flexible polyester cloth for support and mounted into cells designed for electrotransport permeation experiments. The sample side having exposed adhesive was positioned toward the anode. An aqueous donor solution containing 0.1 g/ml metoclopramide was placed on the anode side of the cell. The receptor solution was Dulbecco's phosphate buffered saline (DPBS) at pH 7 and a total salt concentration of about 0.15M. Experiments were conducted at 32° C. for 5 hours. Metoclopramide transport across the adhesive/cloth laminate was measured, both with and without 0.1 mA/cm$^2$ of applied electrical current. The receptor solution was sampled and the cell voltage across the films was monitored every hour. The hydrophobic polymer used was Kendall A200C-0, an acrylate adhesive. The hydrophilic particles were pHEMA, loaded in 20, 30, and 40 weight percent (wt %) amounts. The average particle diameter was within the range of 74-177 μm. Both electrically assisted and passive transport through the Kendall A200C-0/pHEMA adhesives was high, exceeding 1 mg/cm$^2$-hr, thus establishing that the adhesives presented minimal mass transport resistance.

EXAMPLE II

Several adhesive films according to this invention were solvent cast and tested in vitro (32° C.) to measure the cell potential during electrically assisted transport of metoclopramide. The aqueous donor solution contained 0.1 g/ml metoclopramide and the receptor solution was 0.15M DPBS at pH 7. The cells had an anodic polarity and were run at a current of 0.1 mA/cm$^2$. The films tested were comprised of 70 wt % hydrophobic polymer and 30 wt % hydrophilic particles. The polymers tested were silicone adhesive and the acrylate adhesives GELVA 788 and GELVA 737. The hydrophilic particles tested were LHPC having an average particle diameter of <63 μm. Films comprised solely of hydrophobic polymer were also tested. The potentials across each cell and the equivalent resistances are presented in the following table:

TABLE I

| Adhesive | Potential, volts | Resistivity kohm-cm$^2$ | Resistivity, kohm-cm$^2$/mil | Thickness, mils |
| --- | --- | --- | --- | --- |
| Silicone Adhesive/LHPC | 0.084 | 0.84 | 0.28 | 3 |
| GELVA 788/LHPC | 0.024 | 0.24 | 0.10 | 2.5 |

TABLE I-continued

| Adhesive | Potential, volts | Resistivity kohm-cm$^2$ | Resistivity, kohm-cm$^2$/mil | Thickness, mils |
| --- | --- | --- | --- | --- |
| GELVA 737/LHPC | 0.016 | 0.16 | 0.05 | 3 |
| Silicone Adhesive | >30 | >200 | >100 | 2 |
| GELVA 788 | 4.6 | 46 | 18 | 2.5 |
| GELVA 737 | 3 | 30 | 20 | 1.5 |

As is evidenced by the foregoing table, the adhesives of this invention exhibit resistivities well within the acceptable range of less than 0.33 kohm-cm$^2$ per mil thickness of adhesive, and therefore have low voltage requirements during use.

EXAMPLE III

Several adhesive films having an approximate thickness of 3 mils were made according to this invention, having a composition of 70 wt % hydrophobic polymer (silicone adhesive, GELVA 788 and GELVA 737) and 30 wt % hydrophilic particles (PVA, avg. particle diameter of <63 μm). These adhesives were solvent cast, adhered to human cadaver skin and tested as in Example II. Two samples of each adhesive were run. The electrically assisted flux using 0.1 mA/cm$^2$(averaged for the two samples) for metoclopramide versus time is plotted in the FIGURE and the voltages across each cell are presented in the following table:

TABLE II

| Adhesive | Cell Voltage | |
| --- | --- | --- |
|  | Sample 1 | Sample 2 |
| Skin only | 1.59 | 0.83 |
| Skin + Silicone Adhesive/PVA | 0.66 | 0.75 |
| Skin + GELVA 788/PVA | 0.75 | 0.81 |
| Skin + GELVA 737/PVA | 1.20 | 1.50 |

This data establishes that the flux across skin does not change appreciably when the adhesive of this invention is added. This is desirable as the adhesive should not present a significant barrier to mass transport. The data also indicates that the voltage across the skin does not significantly change when the adhesive of this invention is placed on the skin. Therefore, the presence of the adhesive does not create any more electrical resistance than the skin itself does.

EXAMPLE IV

The acrylate-based adhesives of Example I were also tested as to their electrical resistance. The resistance of the Kendall A200C-0/pHEMA adhesives were on the order of 1 kohm-cm$^2$. The electrical resistance of the neat adhesive was approximately 15 kohm-cm$^2$.

EXAMPLE V

Several adhesive film compositions were evaluated for current distribution characteristics. The hydrophobic polymers used were silicone adhesive alone and with silicone medical fluid and the acrylate adhesives GELVA 788 and GELVA 737. The hydrophilic particles were either LHPC or PVA, having an average particle diameter of <63 μm. The adhesives were directly cast in thicknesses of approximately 3 mils onto copper foil and mounted as the anode in an electrochemical cell. The cathode was Ag/AgCl and the electrolyte solution was 0.1M copper sulfate/0.5M sulfuric acid/0.01M sodium chloride solution. The test was run at room temperature for 6 hours at a current density of 0.5 mA/cm². As current flows, copper metal is oxidized underneath the adhesive film. At the conclusion of the experiment, the adhesive was dissolved from the copper foil and the surface of the foil inspected for uniformity of copper dissolution. The following data was obtained where hydration time was the time to reach 75% of the steady state voltage.

TABLE III

| Silicone Adhesive | Silicone Med. fluid | GELVA 788 | GELVA 737 | LHPC | PVA | Hydration Time, hours | Avg Steady State Cell Voltage |
|---|---|---|---|---|---|---|---|
| 80 | | | | 20 | | <3.1 | 0.22 |
| 70 | | | | 30 | | <1 | 0.123 |
| | | 70 | | 30 | | <0.25 | 0.202 |
| | | | 70 | 30 | | <0.25 | 0.2 |
| | | 60 | | 40 | | <0.1 | 0.13 |
| | | | 60 | 40 | | <0.25 | 0.11 |
| 67.5 | 2.5 | | | 30 | | <1.6 | 0.18 |
| 57.5 | 2.5 | | | 40 | | <1 | 0.1 |
| 55 | 5 | | | 40 | | <1 | 0.11 |
| 80 | | | | | 20 | <0.5 | 0.31 |
| 70 | | | | | 30 | <0.25 | 0.15 |
| | | 70 | | | 30 | <0.25 | 0.12 |
| | | | 70 | | 30 | <0.5 | 0.48 |
| 67.5 | 2.5 | | | | 30 | <0.5 | 0.14 |

While lower voltages are preferable, this is not always an indication of a better adhesive film since a low voltage (resistance) may be due to the presence of isolated defects in the adhesive, where all the current could pass through a small area rather than being uniformly distributed over the entire surface of the adhesive. The silicone adhesive formulations exhibited lower overall steady state voltages but showed spots of high current density. The acrylate adhesives showed a more uniform current distribution pattern and shorter hydration times, with the steady state voltages of GELVA 788 being somewhat greater than those of GELVA 737.

EXAMPLE VI

Electrochemical dissolution of a metal in intimate contact with a polymeric film occurs at the aqueous pathways. Therefore, the electrical current distribution across an adhesive is revealed by observing the dissolution pattern created on a metal foil covered or coated by an adhesive. An 80 wt % Kendall A200C-0/20 wt % pHEMA (avg. particle diameter within the range of 74–177 μm) adhesive film was cast onto copper foil (0.0025 mm thick) to a dried film thickness of 5 mils. The copper/adhesive laminate was then mounted as the anode in an electrochemical cell. The cathode was Ag-/AgCl and a 0.5M sulfuric acid/0.01M sodium chloride solution was used as the electrolyte solution. Triplicate samples of copper/adhesive were evaluated for 1, 4, 8 and 24 hours using a current of 0.1 mA/cm². An uncoated copper foil was also included for each set of samples. Following dissolution, the samples were rinsed with water, the adhesive layer was dissolved using methylene chloride, and the dissolution pattern on the copper surface was observed. Between 1 and 8 hours, no holes had formed on the coated sample, but the surface was sprinkled with minute dark spots, no larger than the diameter of a pin, which probably consisted of copper oxide. In contrast, the uncoated sample was uniformly discolored. After 24 hours, randomly dispersed holes (pinhole size or smaller) were observed on the coated sample. After 24 hours, discoloration of the uncoated sample was uniform, but darker than at 8 hours. Comparison of the dissolution patterns of the adhesive coated and uncoated foil samples indicated that the electrical current distribution across the adhesive was adequately distributed across the surface as evidenced by the random dispersion of pits and holes. Increasing the loading of pHEMA and decreasing the particle size will improve the current distribution since that will increase the density of aqueous pathways per unit area.

EXAMPLE VII

Several acrylate-based adhesive formulations were tested as to tack or "stickiness" Kendall A200C-0 was loaded with 20, 30 and 40 wt % pHEMA (avg. particle diameter within the range of 74–177μ). All three films were tacky. Tack was highest for the film with 20 wt % pHEMA and lowest for the film with 40 wt % pHEMA. Additionally, formulations containing silicone adhesive, GELVA 788 and GELVA 737 were compared. All formulations tested exhibited sufficient tack and elasticity for use in an electrotransport transdermal system.

EXAMPLE VIII

Prolonged adhesion to the skin was evaluated using ½" diameter patches consisting of 70 wt % Kendall A200C-0/30 wt % pHEMA (avg. particle diameter within the range of 74–177 μm) films laminated to flexible polyester cloth backing (non-occlusive) and to ethylene vinylacetate coated polyester film (occlusive). These patches were worn on the arm by several subjects. After 7 hours, the patches were still adhering to the skin. No difference in wearability was observed regardless of which backing material was used.

EXAMPLE IX

Several adhesive formulations according to this invention were solvent cast as approximately 3 mil thick films having a disc area of 11.4 cm². The total water uptake was then evaluated, as measured by the total water absorbed (% dry basis). The adhesive compositions tested were comprised of 70 wt % hydrophobic polymer and 30 wt % hydrophilic particles having an average particle diameter of 63μ. The particles tested were LHPC (equilibrium moisture content=20.5% at 95% relative humidity), PVA (equilibrium moisture content=34.5% at 95% relative humidity) and PAA. The hydrophobic polymers tested were silicone adhesive, GELVA 788 and GELVA 737. The experimental conditions were 32° C. with a relative humidity of 95% (sat. salt: $Na_2HPO_4+7H_2O$).

TABLE IV

| Hydrophilic Particles | Hydrophobic Polymer | Time, hrs | Total Water Absorbed % of particle wt | % of adhesive wt |
|---|---|---|---|---|
| — | Sil. Adhesive | 8 | 0 | 0 |
|  | GELVA 788 | 8 | 0 | 0 |
|  | GELVA 737 | 8 | 0 | 0 |
| LHPC | Sil. Adhesive | 8.5 | 12.5 | 3.8 |
|  | GELVA 788 | 8.5 | 23.0 | 6.9 |
|  | GELVA 737 | 8.5 | 19.5 | 5.3 |
| PVA | Sil. Adhesive | 8.2 | 21.0 | 6.3 |
|  | GELVA 788 | 8.2 | 20.5 | 6.2 |
|  | GELVA 737 | 8.2 | 19.5 | 5.9 |
| PAA | Sil. Adhesive | 8.2 | 51 | 15.3 |
|  | GELVA 788 | 8.2 | 60 | 18.0 |
|  | GELVA 737 | 8.2 | 59 | 17.7 |

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An ion-conducting adhesive for adhering an electrotransport agent delivery system to human skin wherein a water soluble and ionized beneficial agent is transported with electrical assistance, comprising a hydrophobic polymer and about 10 to 60 dry weight percent of hydrophilic particles uniformly dispersed therethrough, said particles providing water sorbable pathways for passage of said agent, said hydrophilic particles being comprised of a material selected from the group consisting of gels and ion-exchange resins.

2. The adhesive of claim 1 wherein said particles comprise 30–40 dry weight percent.

3. The adhesive of claim 1 which is capable of absorbing water within the range of 7–80% of the total adhesive weight.

4. The adhesive of claim 1 wherein said adhesive contains at least a portion of the beneficial agent being delivered by the electrotransport agent delivery system.

5. The adhesive of claim 4 wherein said adhesive contains a sufficient amount of the beneficial agent to maintain therapeutic delivery of the beneficial agent from the adhesive for an extended period of time.

6. The adhesive of claim 4, wherein said adhesive contains a sufficient amount of the beneficial agent to provide a loading dose of the beneficial agent.

7. An ion-conducting adhesive suitable for adhering an electrotransport agent delivery system to human skin wherein water soluble and ionized agents are transported with electrical assistance, comprising a hydrophobic polymer and hydrophilic particles uniformly dispersed therethrough, said particles providing water sorbable pathways for passage of said agent, the hydrophilic particles being present in an amount sufficient to enable the adhesive to absorb water in an amount of about 7 to 80% of the total adhesive weight, said hydrophilic particles being comprised of a material selected from the group consisting of gels and ion-exchange resins.

8. The adhesive of claim 7 wherein said particles comprise 10–60 dry weight percent.

9. The adhesive of claim 1 or 7 wherein said particles are comprised of a material selected from the group consisting of polyacrylamide, cross-linked dextran, polyvinylalcohol, starch-graft-poly(sodium acrylate-co-acrylamide) polymers, cellulosic derivatives and hydrogels.

10. The adhesive of claim 9, wherein the cellulosic derivative is selected from the group consisting of hydroxypropylmethylcellulose, low-substituted hydroxypropylcellulose, and cross-linked Na-carboxymethylcellulose.

11. The adhesive of claim 9, wherein the hydrogel is selected from the group consisting of polyhydroxyethyl methacrylate, blends of polyoxyethylene and polyethylene glycols with polyacrylic acid, and cross-linked polyvinyl pyrrolidone.

12. The adhesive of claim 9 wherein said particles have a diameter up to 177 μm.

13. The adhesive of claim 9 wherein said particles have a diameter up to 35 μm.

14. The adhesive of claim 1 or 7 which has a resistivity less than 0.33 kohm-$cm^2$ per mil thickness of adhesive.

15. The adhesive of claim 1 or 7 wherein said hydrophobic polymer has adhesive properties.

16. The adhesive of claim 15 wherein said polymer is selected from the group consisting of acrylate adhesives and silicone adhesives.

17. The adhesive of claim 1 or 7 wherein said hydrophobic polymer is rendered adhesive by the addition of a tackifying resin.

18. The adhesive of claim 17 wherein said adhesive is selected from the group consisting of poly(styrene-butadiene) and poly(styrene-isoprene-styrene) block copolymers, ethylene vinyl acetate polymers, plasticized and unplasticized polyvinylchloride, natural and synthetic rubber, $C_2$–$C_4$ olefins, polyethylene, polyisoprene, polyisobutylene and polybutadiene.

19. The adhesive of claim 17 wherein said tackifying resin is selected from the group consisting of fully hydrogenated aromatic hydrocarbon resins, hydrogenated esters and low molecular weight grades of polyisobutylene.

20. The adhesive of claim 1 or 7 wherein said adhesive when ready for use, is in a dry state.

21. The adhesive of claim 1 or 7 wherein said adhesive when ready for use, is in a hydrated state.

22. The adhesive of claim 1 or 7, wherein the ion-exchange resin comprises a cross-lined dextran.

* * * * *